US009597191B2

(12) United States Patent
Muir et al.

(10) Patent No.: US 9,597,191 B2
(45) Date of Patent: *Mar. 21, 2017

(54) HUMERAL TRIAL AND IMPLANT ASSEMBLY AND METHOD OF USE

(71) Applicant: Biomet Manufacturing, LLC, Warsaw, IN (US)

(72) Inventors: Nicholas Muir, Winona Lake, IN (US); Nathan Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/678,071

(22) Filed: Apr. 3, 2015

(65) Prior Publication Data
US 2016/0287400 A1 Oct. 6, 2016

(51) Int. Cl.
*A61F 2/40* (2006.01)
*A61F 2/46* (2006.01)
*A61F 2/30* (2006.01)

(52) U.S. Cl.
CPC .......... *A61F 2/4014* (2013.01); *A61F 2/4684* (2013.01); *A61F 2/40* (2013.01);
(Continued)

(58) Field of Classification Search
CPC .. A61F 2/40; A61F 2/4014; A61F 2/32; A61F 2/36; A61F 2/3609; A61F 2250/006;
(Continued)

(56) References Cited

U.S. PATENT DOCUMENTS 5,593,448 A * 1/1997 Dong .................... A61F 2/4081
606/86 R
6,589,248 B1 7/2003 Hughes
(Continued)

FOREIGN PATENT DOCUMENTS

DE 320756 C 4/1920
WO WO-2016160417 A1 10/2016
WO WO-2016160444 A1 10/2016

OTHER PUBLICATIONS

STIC search results.*
(Continued)

*Primary Examiner* — David Isabella
*Assistant Examiner* — Dinah Baria
(74) *Attorney, Agent, or Firm* — Schwegman Lundberg & Woessner, P.A.

(57) ABSTRACT

A humeral trial and implant assembly for use in total shoulder arthroplasty is provided along with a method for using the same. The humeral trial and implant assembly includes a humeral fixation component, an adapter assembly, a humeral trial, a humeral implant, and a positioning guide. The humeral trial is coupled to the adapter assembly when the humeral trial and implant assembly is assembled in a trialing configuration. The humeral implant is coupled to the adapter assembly when the humeral trial and implant assembly is assembled in an installed configuration. A temporary connection releasably couples the humeral trial to the adapter assembly and provides separation of the humeral trial and the adapter assembly without requiring disassembly of the adapter assembly. A permanent connection fixedly couples the humeral implant to the adapter assembly. The temporary connection may be a magnetic connection.

20 Claims, 9 Drawing Sheets

(52) U.S. Cl.
CPC ............... *A61F 2002/30079* (2013.01); *A61F 2002/30332* (2013.01); *A61F 2002/30433* (2013.01); *A61F 2002/30434* (2013.01); *A61F 2002/30507* (2013.01); *A61F 2002/30553* (2013.01); *A61F 2002/30617* (2013.01); *A61F 2002/4037* (2013.01); *A61F 2002/4044* (2013.01); *A61F 2002/4062* (2013.01); *A61F 2210/009* (2013.01)

(58) Field of Classification Search
CPC ........ A61F 2210/009; A61F 2002/4018; A61F 2002/4022; A61F 2002/4029; A61F 2002/4037; A61F 2002/4044; A61F 2002/3029; A61F 2002/30672; A61F 2002/3625
USPC ........... 623/19.11, 19.12, 19.14, 22.11, 22.4, 623/22.41, 22.42
See application file for complete search history.

(56) References Cited

U.S. PATENT DOCUMENTS

| | | | |
|---|---|---|---|
| 7,537,618 B2 * | 5/2009 | Collazo | ................ A61F 2/4014 623/19.11 |
| 8,052,758 B1 | 11/2011 | Winslow | |
| 9,510,952 B2 | 12/2016 | Muir et al. | |
| 2003/0187510 A1 | 10/2003 | Hyde | |
| 2004/0186579 A1 | 9/2004 | Callaway et al. | |
| 2009/0192624 A1 | 7/2009 | Collazo | |
| 2009/0216332 A1 | 8/2009 | Splieth et al. | |
| 2010/0049327 A1 | 2/2010 | Isch et al. | |
| 2013/0150975 A1 | 6/2013 | Iannotti et al. | |
| 2013/0197650 A1 | 8/2013 | Smits et al. | |
| 2014/0039636 A1 * | 2/2014 | Kurtz | ..................... A61F 2/389 623/20.32 |
| 2014/0107791 A1 | 4/2014 | Isch et al. | |
| 2016/0287401 A1 | 10/2016 | Muir et al. | |

OTHER PUBLICATIONS

"U.S. Appl. No. 14/678,032, Notice of Allowability mailed Sep. 29, 2016", 2 pgs.
"U.S. Appl. No. 14/678,032, Notice of Allowance mailed Aug. 12, 2016", 12 pgs.
"U.S. Appl. No. 14/678,032, Notice of Allowance mailed Oct. 13, 2016", 8 pgs.
"International Application Serial No. PCT/US2016/023563, International Search Report mailed Aug. 4, 2016", 8 pgs.
"International Application Serial No. PCT/US2016/023563, Written Opinion mailed Aug. 4, 2016", 8 pgs.
"STIC search results", ProQuest NPL.
"STIC search results", ProQuest Patents.
"Application Serial No. PCT/US2016/023712, Invitation to Pay Add'l Fees and Partial Search Report mailed Jun. 3, 2016", 9 pgs.
"International Application Serial No. PCT/US2016/023712, International Search Report mailed Aug. 9, 2016", 9 pgs.
"International Application Serial No. PCT/US2016/023712, Written Opinion mailed Aug. 9, 2016", 11 pgs.

* cited by examiner

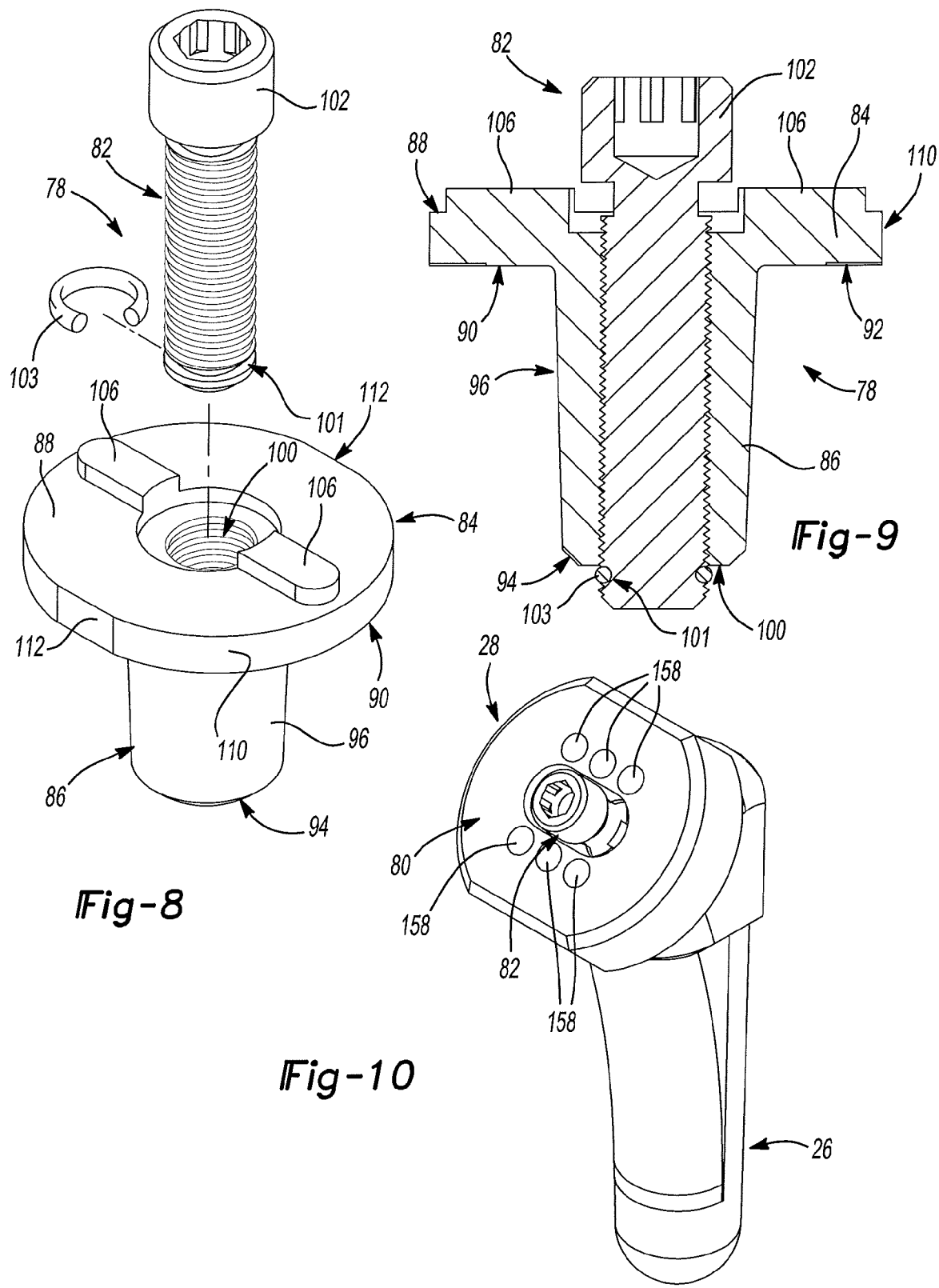

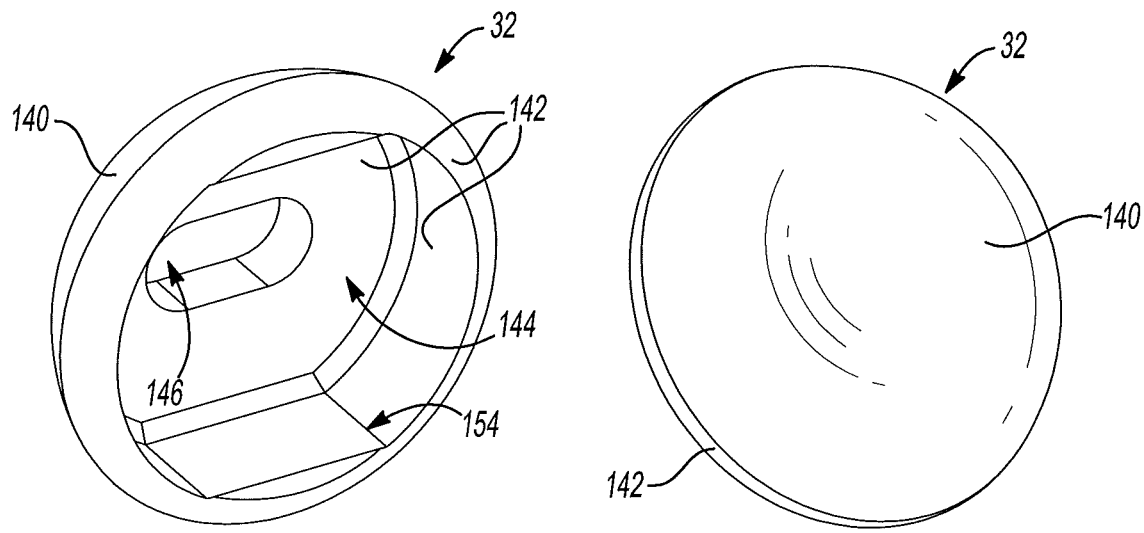
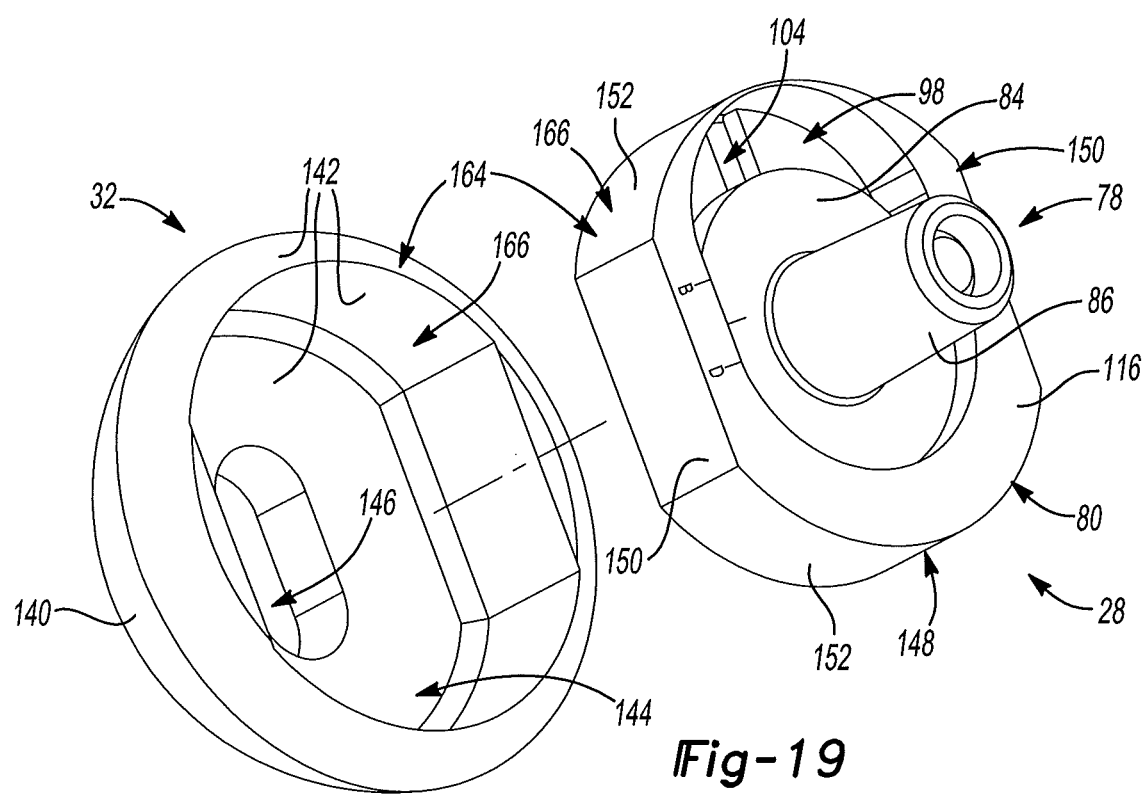

HUMERAL TRIAL AND IMPLANT ASSEMBLY AND METHOD OF USE

FIELD

The subject disclosure relates to the field of humeral trial and implant assemblies for use in total shoulder arthroplasty. More particularly, the subject disclosure relates to anatomically correct humeral trial and implant assemblies. Such humeral trial and implant assemblies are surgically implanted into the shoulder of a patient between the humerus and the glenoid.

BACKGROUND

This section provides background information related to the present disclosure which is not necessarily prior art.

Total shoulder arthroplasty is one of several types of shoulder replacement surgeries. In total shoulder arthroplasty, a portion of a patient's humerus is replaced with implantable components. These components may include a humeral fixation component and a humeral implant. Generally, the humeral fixation component is fixed to the humerus and the humeral implant is coupled to the humeral fixation component. The humeral implant replaces the head of the humerus and thus contacts the patient's glenoid. Accordingly, the surgically created shoulder is anatomically correct, where the "ball" of the shoulder joint is on the humerus side of the shoulder joint. In some surgeries, the glenoid may also be resurfaced with a glenoid resurfacing component that is positioned between the glenoid and the humeral implant.

Because anatomy varies among patients, a surgeon must choose a humeral implant that fits the patient undergoing surgery. To determine proper fit, a humeral trial is used. Before the humeral implant is installed, the surgeon positions the humeral trial on the humeral fixation component. An adapter assembly may be used to couple the humeral trial to the humeral fixation component where a threaded fastener attaches the humeral trial to the adapter assembly. An apical opening is provided in the humeral trial to receive the threaded fastener and to provide access to the head of the threaded fastener. Once the humeral trial is installed on the adapter assembly and is positioned on the humeral fixation component, the surgeon trials the surgically created shoulder joint by moving the humerus through a range of motion. Such trialing allows the surgeon evaluate the fit and function of the humeral trial. If trialing is unsatisfactory, the surgeon must remove the humeral trial from the humeral fixation component and repeat the process with another humeral trial that has a different size and/or shape. This process continues until a satisfactory humeral trial is found.

Once a satisfactory humeral trial is found, the surgeon removes the humeral trial from the humeral fixation component and reads the position of the humeral trial, which is measured relative to the adapter assembly. The surgeon then selects a humeral implant that matches the size and shape of the humeral trial that is selected during the trialing and replicates the position of the humeral trial relative to the adapter assembly when constructing the humeral implant. The humeral implant is then installed on the humeral fixation component and is positioned in contact with either the glenoid or the glenoid resurfacing component to complete the assembly of the surgically created shoulder joint.

While known implants for total shoulder arthroplasty and related implantation methods may have proven to be generally effective, a continuous need for improvement over the pertinent art remains.

SUMMARY

This section provides a general summary of the disclosure, and is not a comprehensive disclosure of its full scope or all of its features.

In accordance with one aspect, the subject disclosure provides a humeral trial and implant assembly for use in total shoulder arthroplasty. The humeral trial and implant assembly includes a humeral fixation component, an adapter assembly, a humeral trial, and a humeral implant. The humeral fixation component is configured to be fixed to a humerus during surgery and includes a primary bore. The adapter assembly includes an adapter and an adapter plate. The adapter has an adapter flange and a body portion that extends from the adapter flange. When the humeral trial and implant assembly is assembled, the body portion of the adapter is received in the primary bore of the humeral fixation component. The humeral trial is coupled to the adapter assembly when the humeral trial and implant assembly is assembled in a trialing configuration. The humeral trial has a medial humeral trial face and a lateral humeral trial face. The medial humeral trial face has a bulbous shape and the lateral humeral trial face defines a humeral trial cavity. The humeral implant is coupled to the adapter assembly when the humeral trial and implant assembly is assembled in an installed configuration. The humeral implant has a medial humeral implant face and a lateral humeral implant face. The medial humeral implant face has a bulbous shape and the lateral humeral implant face defines a humeral implant cavity. The humeral trial and the humeral implant have the same size and shape or substantially the same size and shape such that the bulbous shape of the medial humeral implant face matches the bulbous, shape of the medial humeral trial face.

The adapter plate and the adapter of the adapter assembly are discrete components. When the adapter assembly is assembled, the adapter plate is coupled to the adapter and the adapter plate abuts the adapter flange. When the humeral trial and implant assembly is assembled in the trialing configuration, the adapter plate is received in the humeral trial cavity. On the other hand, when the humeral trial and implant assembly is assembled in the installed configuration, the adapter plate is received in the humeral implant cavity. The humeral trial and implant assembly includes a temporary connection that releasably couples the humeral trial to the adapter assembly when the humeral trial and implant assembly is assembled in the trialing configuration. Advantageously, the temporary connection provides rapid separation of the humeral trial from the adapter assembly without requiring disassembly of the adapter assembly. In some, but not all configurations of the subject humeral trial and implant assembly, the temporary connection may be a magnetic connection between the humeral trial and the adapter assembly. The humeral trial and implant assembly also includes a permanent connection that fixedly couples the humeral implant to the adapter assembly when the humeral trial and implant assembly is assembled in the installed configuration.

In accordance with another aspect, the subject disclosure provides a humeral trial and implant assembly where the adapter assembly has an anti-rotation feature. The adapter includes an adapter bore and the adapter flange has a medial adapter flange face and a lateral adapter flange face. The body portion of the adapter extends from the lateral adapter flange face. The adapter plate abuts the medial adapter flange face when the adapter assembly is assembled. Again, the adapter plate is received in the humeral trial cavity when the humeral trial and implant assembly is in the trialing configuration and the adapter plate is received in the humeral implant cavity when the humeral trial and implant assembly is in the installed configuration. The adapter plate has a medial adapter plate face and a lateral adapter plate face, where the lateral adapter plate face includes a locking channel that extends inwardly into the adapter plate toward the medial adapter plate face. The adapter includes an engagement member that projects from the medial adapter flange face. The engagement member of the adapter is received in and engages the locking channel of the adapter plate when the adapter assembly is assembled. Advantageously, the locking channel and the engagement member cooperate to prevent rotation of the adapter plate relative to the adapter when the humeral trial and implant assembly is in the trialing configuration and when the humeral trial and implant assembly is in the installed configuration.

In accordance with yet another aspect of the subject disclosure, a method of using the subject humeral trial and implant assembly in total shoulder arthroplasty is provided. The method has a number of steps, including: installing the humeral fixation component on the humerus, assembling the adapter assembly by installing the adapter plate on the adapter, inserting the body portion of the adapter into the primary bore in the humeral fixation component, placing the humeral trial over the adapter plate of the adapter assembly, positioning the humeral trial adjacent an associated glenoid, and moving the humerus through a range of motion. As the humerus is moved through the range of motion, the method includes observing the fit and function of the humeral trial. From the observations made during this step, the method includes determining whether the humeral trial is of appropriate size. The method further includes the steps of: separating the adapter assembly and the humeral fixation component by removing the body portion of the adapter from the primary bore of the humeral fixation component, removing the humeral trial from the adapter plate without disassembling the adapter assembly, installing the humeral implant on the adapter plate of the adapter assembly, re-inserting the body portion of the adapter into the primary bore of the humeral fixation component, and positioning the humeral implant adjacent the associated glenoid.

Several benefits are thus realized by the subject humeral trial and implant assembly and the associated method. One benefit is reduced surgery time when compared to other humeral trial and implant assemblies. Because the temporary connection between the humeral trial and the adapter assembly allows the humeral trial to be changed out without requiring disassembly of the adapter assembly, humeral trials may be changed out more rapidly. Another benefit associated with the temporary connection between the humeral trial and the adapter assembly is that a threaded fastener is not used to retain the humeral trial on the adapter. Accordingly, the humeral trial can be provided without the apical opening associated with the humeral trials used in other humeral trial and implant assemblies. Advantageously, the smooth and continuous surface of the humeral trial provides a better approximation of the humeral implant. Yet another benefit provided by the subject humeral trial and implant assembly is that the adapter assembly may be used to couple both the humeral trial and the humeral implant to the humeral fixation component and can be interchanged for this purpose without disassembly. Because the temporary connection allows the adapter assembly to be removed from the humeral trial without disassembling of the adapter assembly and because the locking channel and the engagement member cooperate to prevent rotation of the adapter plate about the adapter, the positioning of the adapter plate relative to the adapter can be maintained. Therefore, the adapter assembly can simply be switched over to the humeral implant and the surgeon does not need to read the position of the adapter plate during trialing and then attempt to replicate that position when constructing the humeral implant. This also reduces surgery time and eliminates errors associated with the reading of the position of the adapter plate during trialing and the re-creation of the position in the humeral implant.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 8 is an exploded front perspective view of the exemplary adapter shown in FIG. 7;

FIG. 9 is a cross-sectional view of the exemplary adapter taken along line 9-9 in FIG. 7;

FIG. 10 is a front perspective view of the exemplary adapter assembly of FIG. 5 shown installed on the humeral fixation component of FIG. 2;

FIG. 17 is a rear perspective view of an exemplary humeral implant of the exemplary humeral trial and implant assembly shown in FIG. 1;

FIG. 18 is a front perspective view of the exemplary humeral implant shown in FIG. 17;

FIG. 19 is a partially exploded rear perspective view of the exemplary adapter assembly of FIG. 5 and the exemplary humeral implant of FIG. 17;

DETAILED DESCRIPTION

Figure 1:
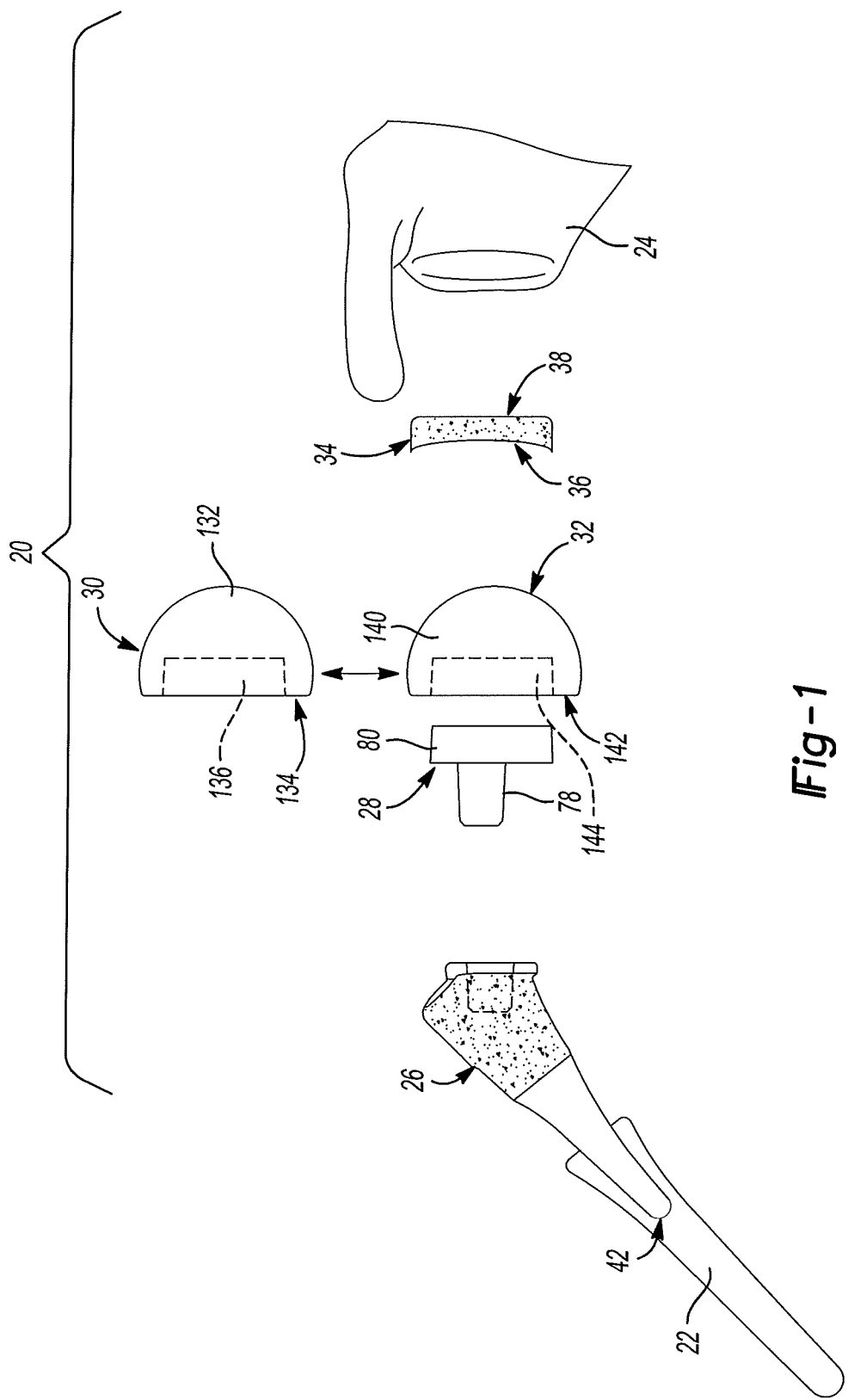
FIG. 1 is an exploded side elevation view of an exemplary humeral trial and implant assembly constructed in accordance with the subject disclosure, where the exemplary humeral trial and implant assembly is shown disposed between an exemplary humerus and glenoid.

Referring to the figures, wherein like numerals indicate corresponding parts throughout the several views, a humeral trial and implant assembly 20 is illustrated. It should be appreciated that the disclosed humeral trial and implant assembly 20 generally falls into the categories of surgical implant assemblies and surgical implant kits. Therefore, the word "assembly" in "humeral trial and implant assembly 20" may be replaced with the word "kit" without departing from the scope of the present disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as "abutting" or being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The humeral trial and implant assembly 20 set forth herein may generally be used in shoulder joint replacement, shoulder resurfacing procedures, and other procedures related to the shoulder joint or the various bones of the shoulder joint, including the glenoid face or cavity of the scapula, the humeral head and adjacent shoulder bones. More particularly, the present teachings may be applied to anatomically correct shoulder replacements, where the head or ball of the shoulder is disposed on the humerus. This stands in contrast to reverse shoulder replacements where the head or ball of the shoulder is disposed on the glenoid. The humeral trial and implant assembly 20 may include conventional implant components and/or patient-specific implant components and/or bone grafts that are prepared using computer-assisted image methods according to the present teachings. Computer modeling for obtaining three-dimensional images of the patient's anatomy using medical scans of the patient's anatomy (such as MRI, CT, ultrasound, X-rays, PET, etc.), the patient-specific prosthesis components and the patient-specific guides, templates and other instruments, can be prepared using various commercially available CAD programs and/or software available, for example, by Object Research Systems or ORS, Montreal, Canada.

The humeral trial and implant assembly 20, when patient-specific, and any associated patient-specific implants and bone grafts can be generally designed and manufactured based on computer modeling of the patient's 3-D anatomic image generated from medical image scans including, for example, X-rays, MRI, CT, PET, ultrasound or other medical scans. Very small irregularities need not be incorporated in the three-dimensional engagement surface. The patient-specific instruments can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting guiding pins, K-wire, or other fasteners according to a surgeon-approved pre-operative plan.

The geometry, shape and orientation of the various elements of the humeral trial and implant assembly 20, as well any patient-specific implants and bone grafts, if used, can be determined during the pre-operative planning stage of the procedure in connection with the computer-assisted modeling of the patient's anatomy. During the pre-operative planning stage, patient-specific instruments, custom, semi-custom or non-custom implants and other non-custom tools, can be selected and the patient-specific components can be manufactured for a specific-patient with input from a surgeon or other professional associated with the surgical procedure. Notwithstanding the foregoing, one of the benefits of the subject humeral trial and implant assembly 20 is that such custom made implants and pre-operative planning is not required due to the use of trialing.

As shown in FIG. 1, the humeral trial and implant assembly 20 is disposed between a humerus 22 and a glenoid 24 of a human body. The humeral trial and implant assembly 20 generally includes a humeral fixation component 26, an adapter assembly 28, a humeral trial 30, and a humeral implant 32. The glenoid 24 and the humerus 22 of the human body generally oppose one another and form part of an anatomical shoulder joint. As noted above, the humeral trial and implant assembly 20 is used to surgically repair the anatomical shoulder joint and more specifically a damaged humerus 22. Thus, the humeral fixation component 26 is installed on/in the humerus 22 and the humeral trial 30, and later the humeral implant 32, abut the glenoid 24. As such, the adapter assembly 28 and either the humeral trial 30 or the humeral implant 32 are disposed between the humeral fixation component 26 and the glenoid 24. It should be appreciated that the humeral trial and implant assembly 20 may be assembled in two different configurations. These two different configurations include a trialing configuration and an installed configuration. As shown in FIG. 1, in both the trialing configuration and in the installed configuration, the humeral fixation component assembly 26 is disposed between the humerus 22 and the adapter assembly 28. In the trialing configuration, the shoulder joint that is surgically repaired by the humeral trial and implant assembly 20 is tested using the humeral trial 30. This humeral trial 30 is a temporary component in the surgically repaired shoulder joint and may be selected from a plurality of humeral trials 30 of varying shapes and sizes. It should be appreciated that the humeral trial 30 may be classified as a "temporary component" in the sense that it is removed after trialing is completed and does not remain as part of the surgically created shoulder joint after completion of the surgery (i.e. post surgery). This stands in contrast to the humeral fixation component 26, for example, which is part of the surgically created shoulder joint during trialing and post surgery. In the installed configuration, the humeral trial 30 is swapped out for the humeral implant 32, which remains part of the surgically created shoulder joint post surgery. Like the humeral trial 30, the humeral implant 32 may be selected from a plurality of humeral implants 32 of varying shapes and sizes. Generally, the humeral implant 32 that is chosen has the same shape and size as the humeral trial 30 that is selected by trialing.

Depending on the material of the humeral implant 32 and the condition of the glenoid 24, the humeral trial and implant assembly 20 may optionally include a glenoid resurfacing component 34. When the material of the humeral implant 32 would wear against the glenoid 24 and/or where the glenoid 24 has been damaged, the glenoid resurfacing component 34 may be applied to the glenoid 24. Therefore, the humeral trial 30 is disposed between the adapter assembly 28 and either the glenoid 24 or the glenoid resurfacing component 34 in the trialing configuration. Similarly, the humeral implant 32 is disposed between the adapter assembly 28 and either the glenoid 24 or the glenoid resurfacing component 34 in the installed configuration.

The subject disclosure includes a naming convention, where the term "medial" means that the associated element is oriented toward or faces the glenoid 24 and where the term "lateral" means that the associated element is oriented toward or faces the humerus 22. The glenoid resurfacing component 34 includes a lateral surface 36 and medial surface 38. When glenoid resurfacing component 34 is applied to the glenoid 24, the medial surface 38 is fixed to the glenoid 24 in an abutting relationship. The glenoid resurfacing component 34 is thus positioned between the glenoid 24 and the humeral trial 30 when the humeral trial and implant assembly 20 is in the trialing configuration such that the lateral surface 36 of the glenoid resurfacing component 34 contacts the humeral trial 30. Similarly, the glenoid resurfacing component 34 is positioned between the glenoid 24 and the humeral implant 32 when the humeral trial and implant assembly 20 is in the installed configuration such that the lateral surface 36 of the glenoid resurfacing component 34 contacts the humeral implant 32. In this way, it should be appreciated that the glenoid resurfacing component 34 acts as a bushing between the glenoid 24 and either the humeral trial 30 or the humeral implant 32 to help prevent wear on the glenoid 24. Accordingly, the glenoid resurfacing component 34 may be selected from a plastic material such as polyethylene, for example. Notwithstanding, the glenoid resurfacing component 34 can be made of a variety of other materials without departing from the scope of the subject disclosure. Where the glenoid resurfacing component 34 is not used, the humeral trial 30 directly contacts the glenoid 24 in the trialing configuration and the humeral implant 32 directly contacts the glenoid 24 in the installed configuration.

Figure 2:
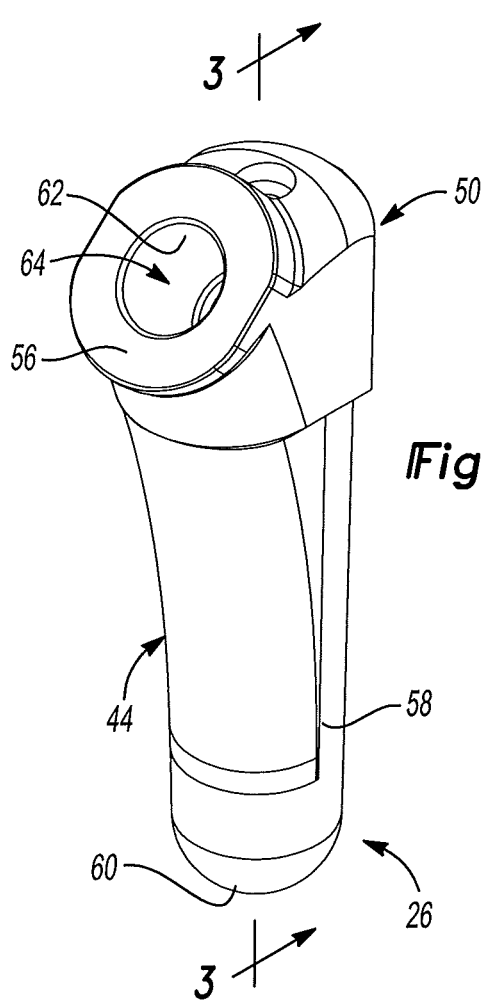
FIG. 2 is a front perspective view of an exemplary humeral fixation component of the exemplary humeral trial and implant assembly shown in FIG. 1.
Figure 3:
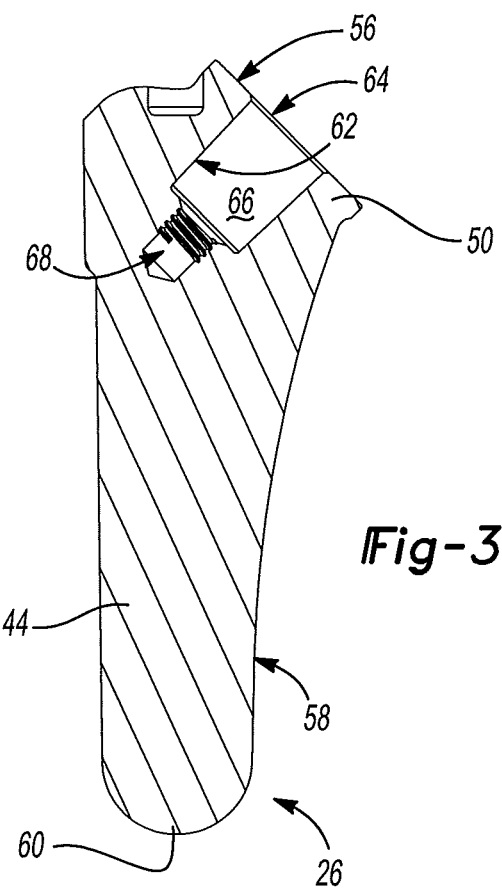
FIG. 3 is a cross-sectional view of the exemplary humeral fixation component taken along line 3-3 in FIG. 2.
Figure 4:
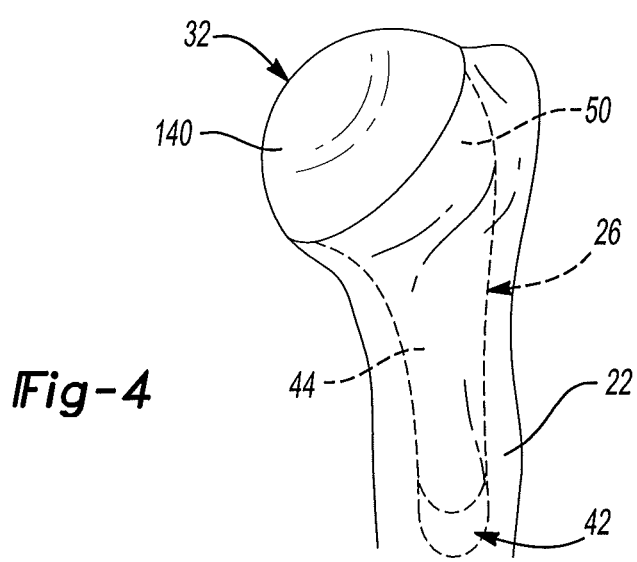
FIG. 4 is a side elevation view of the exemplary humeral fixation component shown in FIG. 2 where the exemplary humeral fixation component is installed on the humerus and a humeral implant is positioned on the exemplary humeral fixation component.

The humeral fixation component 26 is fixedly connected to the humerus 22 during surgery. The humeral fixation component 26 may have a variety of different configurations. In the configuration illustrated in FIGS. 1-4, the humeral fixation component 26 is configured to be implanted into a surgical bore 42 created in the humerus 22. Although the orientation of the surgical bore 42 may vary to some degree, the surgical bore 42 generally extends co-axially within the humerus 22. The humeral fixation component 26, which is shown by itself in FIGS. 2 and 3, includes a stem section 44 and a flange section 50. The flange section 50 has a stem flange face 56, which generally faces the glenoid 24. The stem section 44 of the humeral fixation component 26 has an implantable stem face 58 and extends from the flange section 50 to a stem end 60. During shoulder surgery, the stem end 60 is inserted into the surgical bore 42 and the implantable stem face 58 forms an interference fit with the humerus 22. The implantable stem face 58 may also be provided with a coating or surface treatment that promotes fusion between the implantable stem face 58 and the humerus 22. The flange section 50 includes an interior flange surface 62. The interior flange surface 62 defines a primary bore 64 that extends into the flange section 50 of the humeral fixation component 26. As best seen in FIG. 3, the interior flange surface 62 includes a tapered portion 66 extending to the stem flange face 56 and a throat 68 of reduced diameter that is located further inward. The throat 68 may optionally be threaded as shown in FIG. 3.

Figure 5:
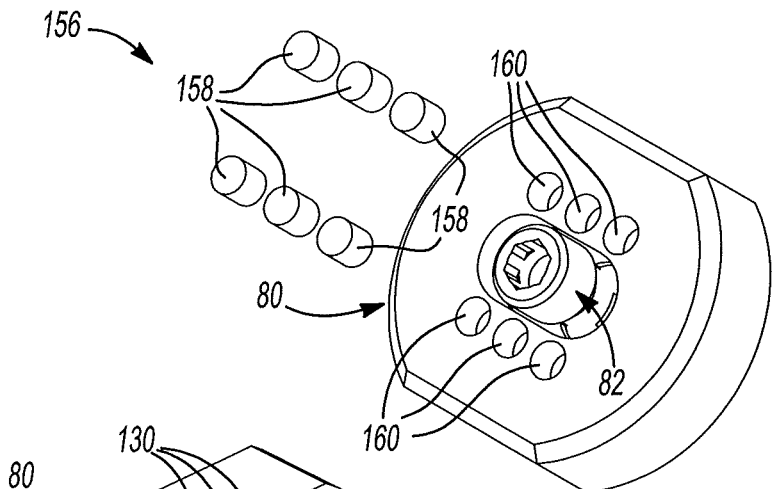
FIG. 5 is a partially exploded front perspective view of an exemplary adapter assembly of the exemplary humeral trial and implant assembly shown in FIG. 1.
Figure 6:
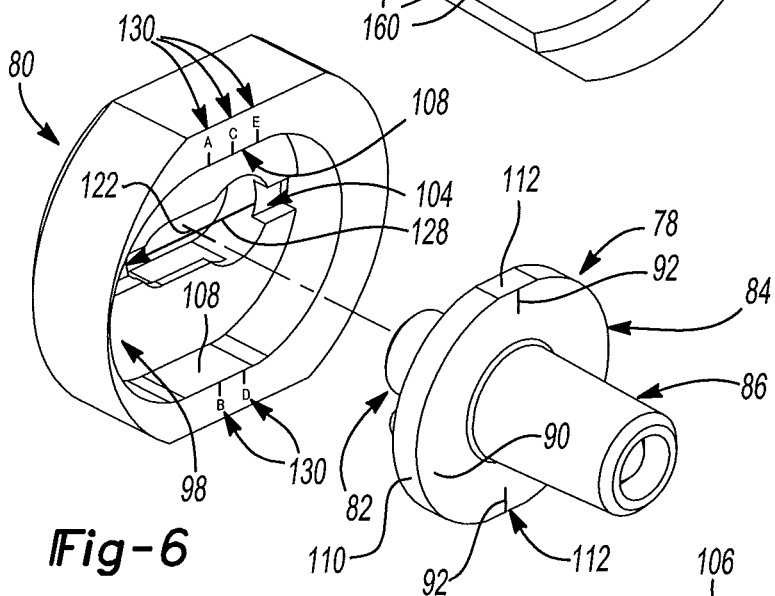
FIG. 6 is a partially exploded rear perspective view of the exemplary adapter assembly shown in FIG. 5.

Referring to FIGS. 5 through 9, the adapter assembly 28 of the humeral trial and implant assembly 20 generally includes an adapter 78, an adapter plate 80, and an adapter fastener 82. The adapter 78 includes an adapter flange 84 and a body portion 86 that extends from the adapter flange 84. The adapter flange 84 presents a medial adapter flange face 88 and a lateral adapter flange face 90. The adapter flange 84 has a cylindrical shape and includes one or more demarcations 92 on the lateral adapter flange face 90 (see FIG. 6). The body portion 86 of the adapter flange 84 extends from the lateral adapter flange face 90 to a lateral body portion end 94. The body portion 86 of the adapter 78 may be generally cylindrical in shape and has a tapered outer surface 96. As best seen in FIG. 6, the adapter plate 80 includes a lateral adapter plate cavity 98 that receives the adapter flange 84 when the adapter assembly 28 is assembled. The adapter 78 includes an adapter bore 100, which may be threaded and that is open to the medial adapter flange face 88. As best seen in FIGS. 8 and 9, the adapter fastener 82, which may be threaded, is received in the adapter bore 100 and includes an adapter fastener head 102 that projects from the medial adapter flange face 88. The adapter fastener head 102 abuts the adapter plate 80 thereby holding the adapter assembly 28 together. The adapter fastener 82 may also include a groove 101 that is spaced from the adapter fastener head 102. The groove 101 may extend annularly and is cut into the adapter fastener 82 such that the adapter fastener 82 has a smaller diameter at the groove 101. During assembly of the adapter assembly, the adapter fastener 82 is inserted (i.e. threaded) far enough into the adapter bore 100 that the adapter fastener 82 extends from the lateral body portion end 94 of the adapter 78 and the groove 101 becomes exposed (i.e. is positioned outside the adapter bore 100 adjacent the lateral body portion end 94). The groove 101 in the adapter fastener 82 receives a retainer 103 that is inserted into the groove 101 and contacts the lateral body portion end 94 of the adapter 78 to prevent removal of the adapter fastener 82 from the adapter bore 100 after assembly. In other words, the groove 101 and the retainer 103 stop the adapter fastener 82 from backing out of the adapter bore 100. While the structure of the retainer 103 may vary from the configuration shown in FIGS. 8 and 9, the retainer 103 may be, for example, a "C" shaped clip.

Figure 7:
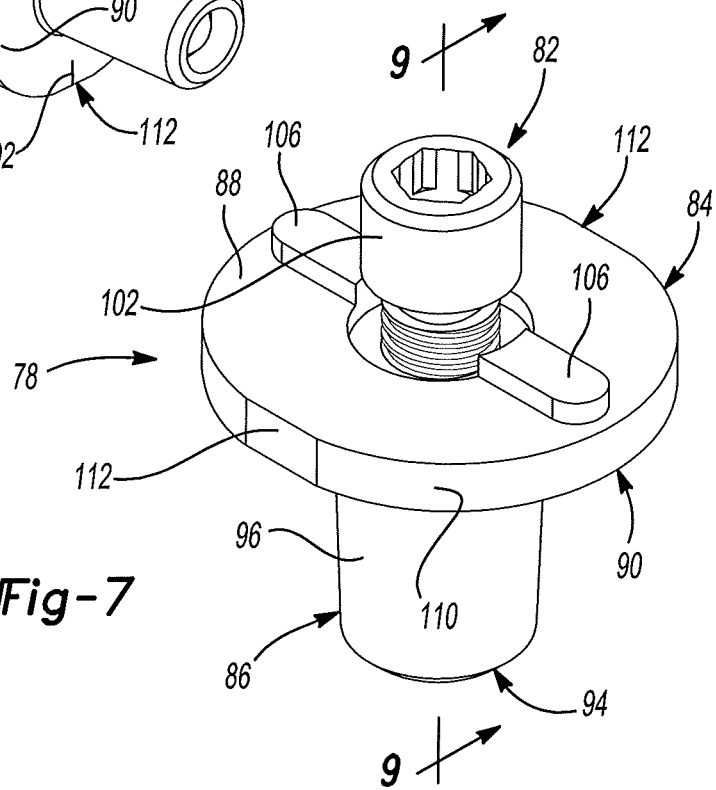
FIG. 7 is a front perspective view of an exemplary adapter of the exemplary humeral trial and implant assembly shown in FIG. 1.

As shown in FIG. 6, the adapter plate 80 includes a locking channel 104 disposed within the lateral adapter plate cavity 98. The locking channel 104 extends further into the adapter plate 80 such as to form a depression within the lateral adapter plate cavity 98. As best seen in FIGS. 7-9, the adapter 78 further includes an engagement member 106 projecting outwardly from the medial adapter flange face 88. When the adapter assembly 28 is assembled, the engagement member 106 of the adapter 78 is received in and engages the locking channel 104 in the adapter plate 80 to rotatably couple the adapter plate 80 with the adapter 78. In other words, the engagement member 106 of the adapter 78 and the locking channel 104 in the adapter plate 80 cooperate to prevent rotation of the adapter plate 80 relative to the adapter 78 when the humeral trial and implant assembly 20 is in the trialing configuration and the installed configuration. The adapter flange 84 may also interface with the lateral adapter plate cavity 98 to help prevent rotation of the adapter plate 80 relative to the adapter 78. For example, FIGS. 6-9 shows that the lateral adapter plate cavity 98 may have one or more planar sides 108 and the adapter flange 84 may have a perimeter 110 that is non-circular. In one configuration, the perimeter 110 of the adapter flange 84 may include one or more flat sections 112 that abut the planar sides 108 of the lateral adapter plate cavity 98. This interface helps prevent rotation of the adapter plate 80 relative to the adapter 78.

With reference to FIGS. 3, 9 and 10, the body portion 86 of the adapter 78 is received in the primary bore 64 of the humeral fixation component 26. As will be explained further in the method set forth below, it is envisioned that the body portion 86 of the adapter 78 will be disposed in the primary bore 64 of the humeral fixation component 26 when the humeral trial and implant assembly 20 is in the trialing configuration and when the humeral trial and implant assembly 20 is in the installed configuration. Generally, the body portion 86 of the adapter 78 may be loosely inserted into the primary bore 64 of the humeral fixation component 26 when the humeral trial and implant assembly 20 is in the trialing configuration so that the adapter assembly 28 can be easily removed or separated from the humeral fixation component 26 for changing out humeral trials 30 or installing the humeral implant 32. The body portion 86 of the adapter 78 may then be firmly pressed into the primary bore 64 of the humeral fixation component 26 when the humeral trial and implant assembly 20 is in the installed configuration so that the adapter assembly 28 will not separate from the humeral fixation component 26. To this end, when the body portion 86 of the adapter 78 is pressed into the primary bore 64 of the humeral fixation component 26, the tapered outer surface 96 of the body portion 86 mates with the tapered portion 66 of the interior fixation stem surface 62. This helps to prevent separation of the adapter 78 and the humeral fixation component 26 when the humeral trial and implant assembly 20 is in the installed configuration.

Figure 11:
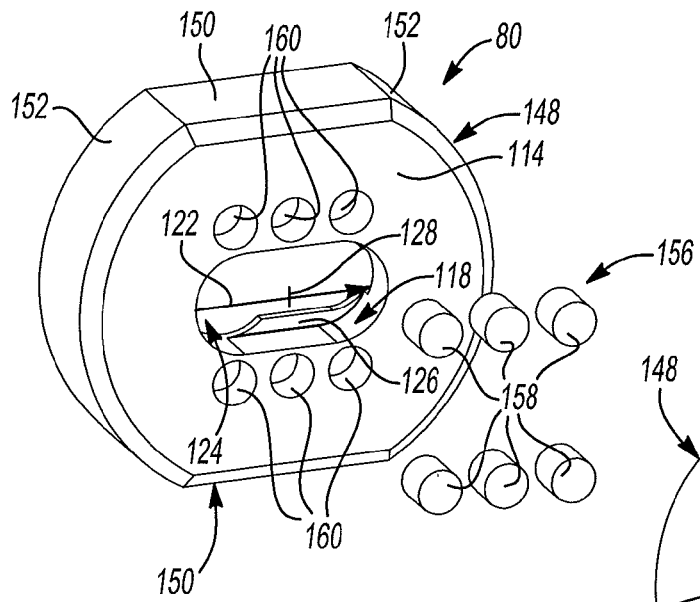
FIG. 11 is an exploded front perspective view of an exemplary adapter plate of the exemplary humeral trial and implant assembly shown in FIG. 1.
Figure 12:
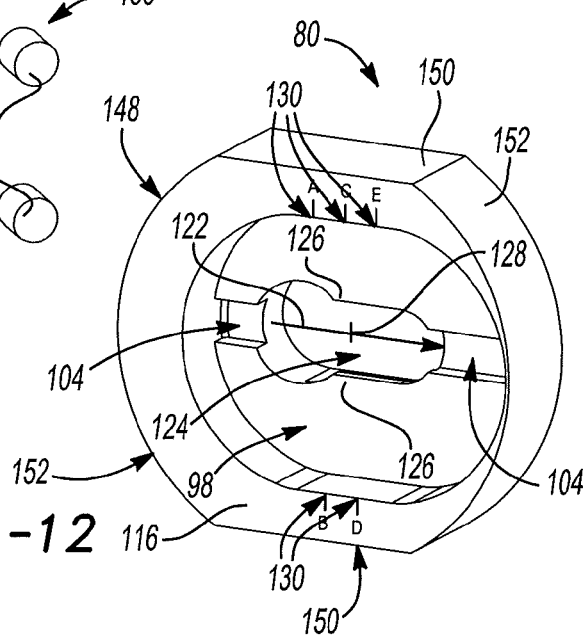
FIG. 12 is a rear perspective view of the exemplary adapter plate shown in FIG. 11.

As shown throughout the views, the adapter plate 80 and the adapter 78 of the adapter assembly 28 are separate, discrete components. When the adapter assembly 28 is assembled as shown in FIGS. 5 and 6, the adapter plate 80 abuts the adapter flange 84 and the adapter fastener 82 couples the adapter plate 80 to the adapter 78. With reference to FIGS. 11 and 12, the adapter plate 80 is shown by itself. The adapter plate 80 has a medial adapter plate face 114 and a lateral adapter plate face 116. The medial adapter plate face 114 defines a medial adapter plate cavity 118 that has a slot-like shape. The lateral adapter plate face 116 defines the lateral adapter plate cavity 98, which receives the adapter flange 84 when the adapter assembly 28 is assembled (see FIG. 6). The lateral adapter plate cavity 98 is larger than the adapter flange 84 and is elongated along an offset direction 122 such that the adapter 78 may be shifted relative to the adapter plate 80 in the offset direction 122 when the humeral trial and implant assembly 20 is in the trialing configuration. The both the locking channel 104 and the engagement member 106 may have a linearly extending shape that is parallel to the offset direction 122. Further still, the planar sides 108 of the lateral adapter plate cavity 98 and the flat sections 112 of the adapter flange 84 may also be parallel to the offset direction 122. Therefore, it should be appreciated that the locking channel 104, the engagement member 106, the planar sides 108, and the flat sections 112 work together to provide a range of adjustment in the offset direction 122 by permitting sliding movement of the adapter plate 80 relative to the adapter 78 along the offset direction 122 while at the same time resisting rotational movement of the adapter plate 80 relative to the adapter 78 when the adapter plate 80 is being slid into position. Advantageously, the range of adjustment this feature provides gives surgeons greater flexibility in locating the humeral trial 30 and later the humeral implant 32. Such flexibility in positioning of the humeral trial 30 and later the humeral implant 32 can be particularly beneficial where anatomical structures, abnormalities, or damage to the shoulder joint limits placement of the humeral fixation component 26 and/or would otherwise interfere with the range of motion of the humerus 22.

The adapter plate 80 includes a pass-through 124 that extends between and that is open to the medial adapter plate cavity 118 and the lateral adapter plate cavity 98. The pass-through 124 may have a key-hole shape. The key-hole shape of the pass-through 124 is created by ribs 126 that that extend into the pass-through 124 and that are disposed between the medial adapter plate cavity 118 and the lateral adapter plate cavity 98. The adapter fastener 82 extends through the pass-through 124 and into the adapter bore 100 to selectively fix the adapter plate 80 to the adapter 78. The pass-through 124 is also elongated along the offset direction 122 such that the adapter 78 may be shifted relative to the adapter plate 80 in the offset direction 122 when the humeral trial and implant assembly 20 is in the trialing configuration. The adapter fastener head 102 can be tightened against the ribs 126 in the pass-through 124 to fix the adapter plate 80 in place relative to the adapter 78 at an offset position 128 located along the offset direction 122. In this way, the offset position 128 of the adapter plate 80 relative to the adapter 78 can be adjusted in the trialing configuration and is then set by tightening the adapter fastener 82. This locks the adapter plate 80 in the offset position 128 that is designated during trialing such that the offset position 128 is maintained when the humeral trial and implant assembly 20 is in the installed configuration. From FIGS. 6-12, it should be appreciated that the locking channel 104 may be aligned with the pass-through 124 such that the locking channel 104 is disposed in the lateral adapter plate cavity 98 on each side of the pass-through 124. Similarly, the engagement member 106 may be aligned with the adapter bore 100 such that the adapter bore 100 splits the engagement member 106 into two segments. In other words, the engagement member 106 may be disposed on each side of the adapter bore 100.

As best seen in FIGS. 6 and 12, the lateral adapter plate face 116 includes a plurality of labeled demarcations 130 adjacent the lateral adapter plate cavity 98 that provide an offset position measurement. The offset position measurement may be determined by identifying which one of the labeled demarcations 130 on the lateral adapter plate face 116 is aligned with one of the demarcations 92 on the lateral adapter flange face 90. The offset position measurement may then be used by the surgeon to set the offset position 128 of the adapter assembly 28 in the installed position, where the same adapter assembly 28 is not used in both the trialing position and the installed position. However, one notable advantage of the adapter assembly 28 described herein over other implant assemblies, is that the disclosed adapter assembly 28 may optionally be used in both the trialing and installed configurations. Therefore, the offset position measurement from the humeral trial 30 need not be replicated for the humeral implant 32 because the adapter assembly 28 from the trialing configuration can simply be reused in the installed configuration. This reduces surgery time and minimizes error because the surgeon does not need to read the offset measurement position and replicate it in the humeral implant 32.

Figure 15:
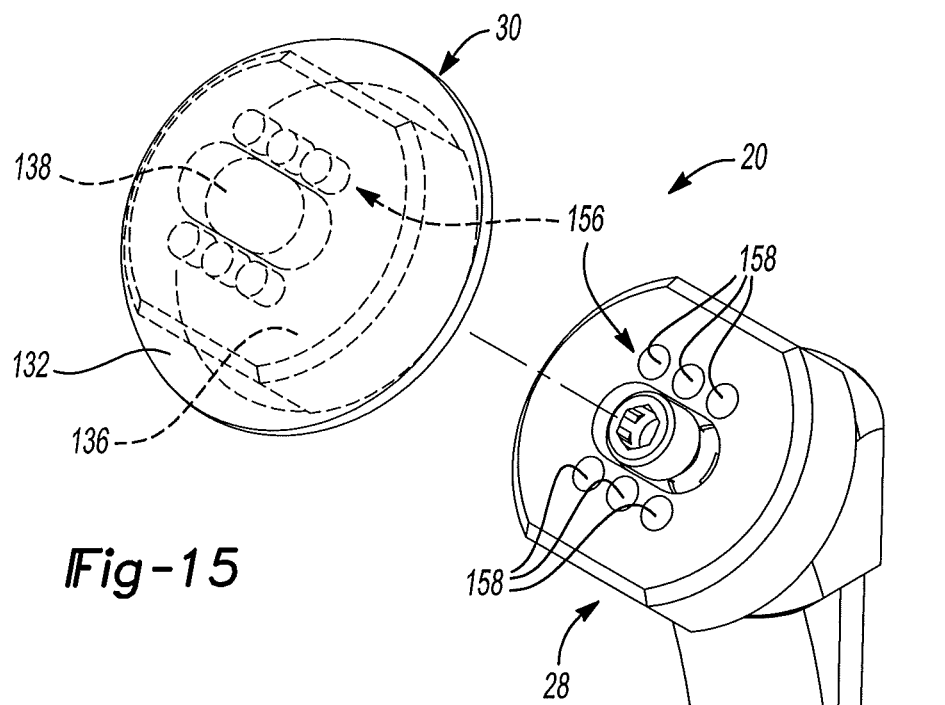
FIG. 15 is a partially exploded front perspective view of the exemplary humeral trial of FIG. 13 and the exemplary adapter assembly of FIG. 5 shown being installed on the humeral fixation component of FIG. 2.
Figure 16:
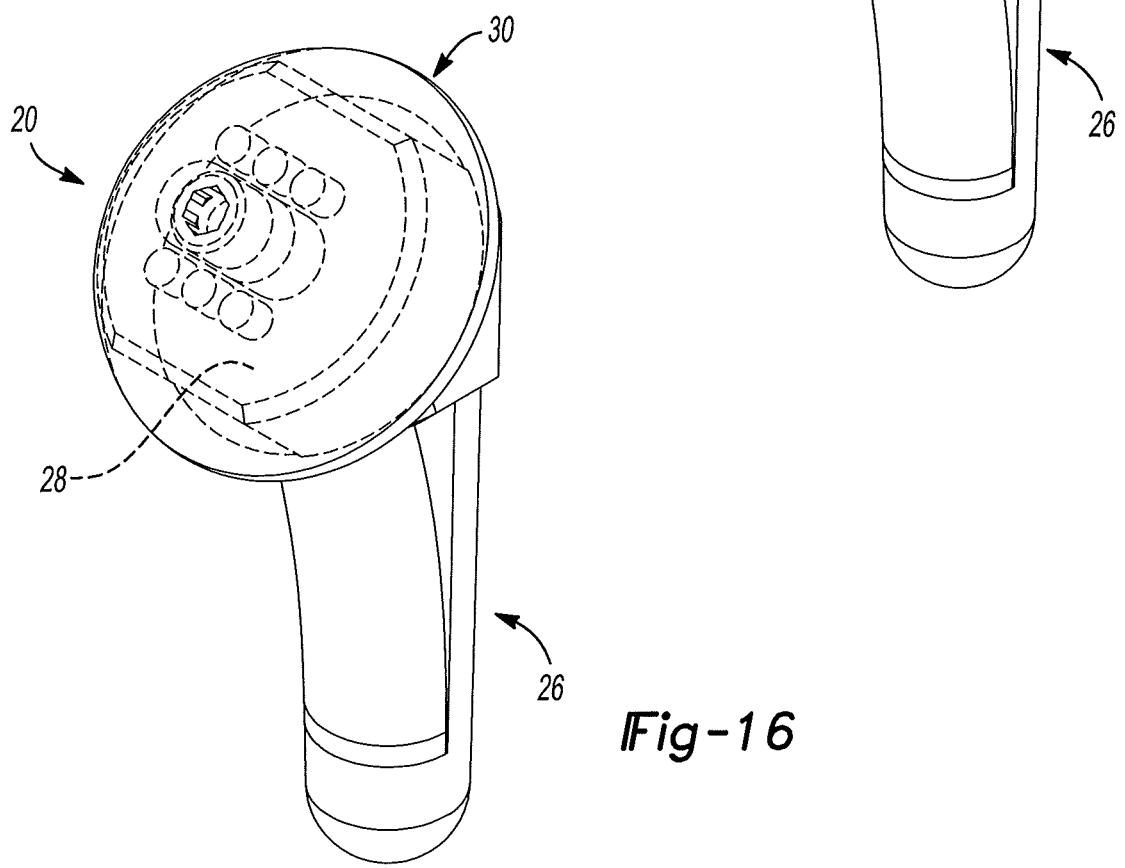
FIG. 16 is a front perspective view of the exemplary humeral trial of FIG. 13 shown installed on the exemplary adapter assembly of FIG. 5 and the humeral fixation component of FIG. 2.

With reference to FIGS. 13-16, the humeral trial 30 is shown. The humeral trial 30 has a medial humeral trial face 132 that has a bulbous shape and a lateral humeral trial face 134 that defines a humeral trial cavity 136. It should be appreciated that the medial humeral trial face 132 abuts either the glenoid 24 itself or the lateral surface 36 of the glenoid resurfacing component 34 (if used) when the humeral trial and implant assembly 20 is in the trialing configuration. To provide clearance for the adapter fastener head 102, the humeral trial cavity 136 may additionally include a first fastener head pocket 138. It should be appreciated that the first fastener head pocket 138 does not extend through the humeral trial 30 to the medial humeral trial face 132. As shown in FIGS. 15 and 16, the humeral trial 30 is temporarily coupled to the adapter assembly 28 and thus the humeral fixation component 26 when the humeral trial and implant assembly 20 is in the trialing configuration. Specifically, the adapter plate 80 of the adapter assembly 28 is received in the humeral trial cavity 136 when the humeral trial and implant assembly 20 is in the trialing configuration. Accordingly, the medial adapter plate face 114 is disposed within the humeral trial cavity 136 adjacent the lateral humeral trial face 134 when the humeral trial and implant assembly 20 is in the trialing configuration. Again, the humeral trial 30 may be selected from a plurality of humeral trials 30 of varying shapes and sizes. For example and without limitation, the bulbous shape of the medial humeral trial face 132 of the different humeral trials 30 may be hemispherical or oblong and may have different dimensions. As will be explained in greater detail below, the humeral trial 30 and the adapter plate 80 are configured such that the humeral trial 30 can be separated from the adapter plate 80 of the adapter assembly 28 in a quick and easy manner. This allows surgeons to rapidly change out different humeral trials 30 until a satisfactory fit is found. It should be appreciated that the glenoid 24 and the glenoid resurfacing component 34 will vary in size depending on the anatomy of the patient. Proper fit of the humeral implant 32 is critical to the integrity, longevity, and range of motion of the surgically repaired shoulder joint so finding the proper humeral trial 30 is an important part of the procedure.

Figure 20:
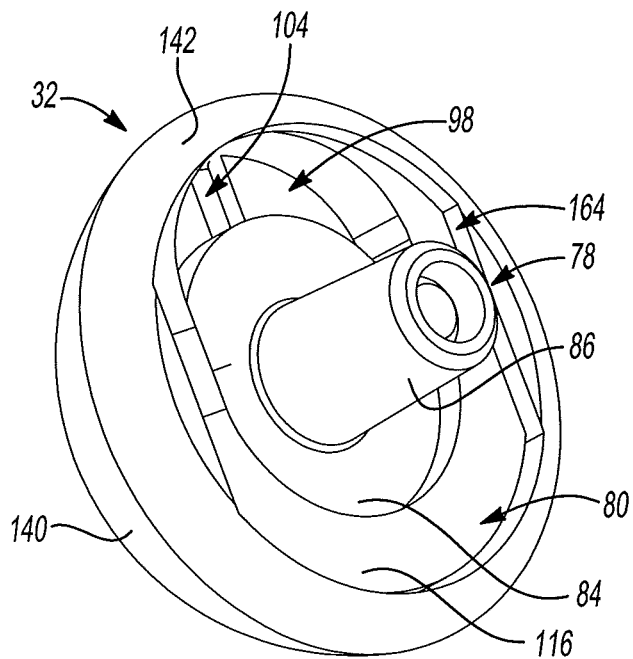
FIG. 20 is a rear perspective view of the exemplary adapter assembly of FIG. 5 shown installed in the exemplary humeral implant of FIG. 17.

With reference to FIGS. 17-20, the humeral implant 32 is shown. The humeral implant 32 has a medial humeral implant face 140 that has a bulbous shape and a lateral humeral implant face 142 that defines a humeral implant cavity 144. It should be appreciated that the medial humeral implant face 140 abuts either the glenoid 24 itself or the lateral surface 36 of the glenoid resurfacing component 34 (if used) when the humeral trial and implant assembly 20 is in the installed configuration. To provide clearance for the adapter fastener head 102, the humeral implant cavity 144 may additionally include a second fastener head pocket 146. It should be appreciated that the second fastener head pocket 146 does not extend through the humeral implant 32 to the medial humeral implant face 140. Again, the humeral implant 32 may be selected from a plurality of humeral implants 32 of varying shapes and sizes. Generally, the humeral implant 32 is selected to have the same shape and size (i.e. dimensions) as the humeral trial 30 that is selected by the surgeon during trialing. Therefore, the bulbous shape of the medial humeral implant face 140 will match the bulbous shape of the medial humeral trial face 132. Unlike the humeral trial 30, the humeral implant 32 is permanently coupled to the adapter assembly 28. As shown in FIGS. 19 and 20, the adapter plate 80 of the adapter assembly 28 is received in the humeral implant cavity 144 when the humeral trial and implant assembly 20 is in the installed configuration. Accordingly, the medial adapter plate face 114 is disposed in the humeral implant cavity 144 adjacent the lateral humeral implant face 142 when the humeral trial and implant assembly 20 is in the installed configuration. The humeral implant 32 and adapter assembly 28 are then installed on the humeral fixation component 26 by pressing the body portion 86 of the adapter 78 into the primary bore 64 of the humeral fixation component 26. This press-fit connection may rotationally fix the adapter 78 in place relative to the humeral fixation component 26 and prevents separation of the adapter 78 from the humeral fixation component 26 post surgery.

Figure 13:
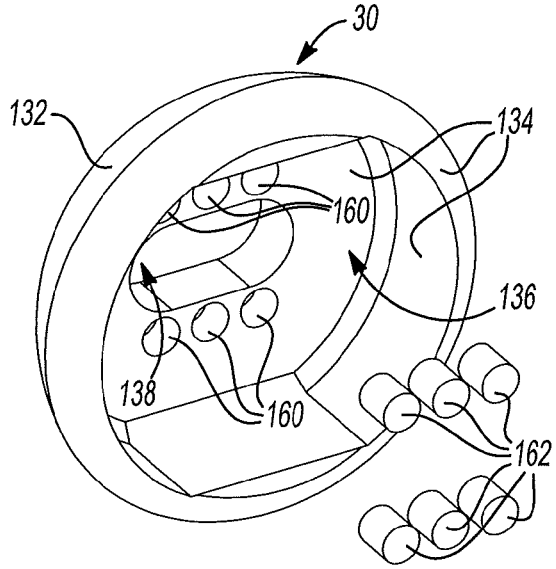
FIG. 13 is an exploded rear perspective view of an exemplary humeral trial of the exemplary humeral trial and implant assembly shown in FIG. 1.
Figure 14:
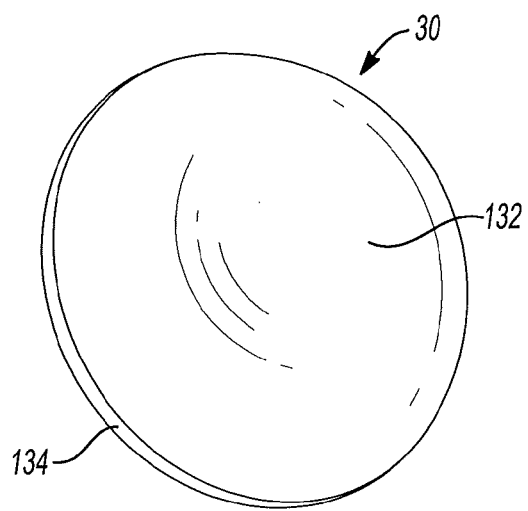
FIG. 14 is a front perspective view of the exemplary humeral trial shown in FIG. 13.

When the humeral trial and implant assembly 20 is in the trialing configuration and when the humeral trial and implant assembly 20 is in the installed configuration, the lateral adapter plate face 116 abuts the stem flange face 56. Additionally, the adapter fastener head 102 is entirely covered by the humeral trial 30 in the trialing configuration and is entirely covered by the humeral implant 32 in the installed configuration. As best seen in FIGS. 11 and 12, the adapter plate 80 includes a periphery 148 having a non-circular shape. Although the non-circular shape of the periphery 148 may take a variety of different forms, the periphery 148 of the adapter plate 80 illustrated includes a pair of opposing flat faces 150 that are spaced by a pair of opposing curved faces 152. As best seen in FIGS. 13 and 17, the humeral trial cavity 136 and the humeral implant cavity 144 both have a geometry 154 that corresponds to the non-circular shape of the periphery 148. This geometric relationship prevents the humeral trial 30 from rotating with respect to the adapter plate 80 when the adapter plate 80 is received within the humeral trial cavity 136. Similarly, the humeral implant 32 cannot rotate with respect to the adapter plate 80 when the adapter plate 80 is received within the humeral implant cavity 144 in the installed configuration. When combined with the locking channel 104 and the engagement member 106, the humeral implant 32 is rotationally fixed with respect to the adapter 78 and thus the humeral fixation component 26 in the installed configuration. However, the humeral trial 30 may be rotated with respect to the humeral fixation component 26 during trialing.

With reference to FIGS. 13-16, a temporary connection 156 releasably couples the humeral trial 30 to the adapter assembly 28. The temporary connection 156 allows for rapid separation of the humeral trial 30 from the adapter assembly 28 without requiring disassembly of the adapter assembly 28. Because separation can occur without disassembly of the adapter assembly 28, the temporary connection 156 allows for the rapid separation of the humeral trial 30 and adapter assembly 28 while maintaining or preserving the offset position 128 of the adapter plate 80 relative to the adapter 78. The offset position 128 is preserved because the humeral trial 30 can be removed without loosening the adapter fastener 82. As the term is used herein, "temporary connection" encompasses any connection between the humeral trial 30 and the adapter assembly 28 that can be released, severed, separated, disconnected, or decoupled without requiring disassembly of the adapter assembly 28. For example and without limitation, such a temporary connection 156 could include a magnetic connection between the humeral trial 30 and the adapter assembly 28, threads disposed on the humeral trial cavity 136 and the periphery 148 of the adapter plate 80, a removable clip interconnecting the humeral trial 30 and the adapter assembly 28, or a tongue and groove connection between the humeral trial 30 and the adapter assembly 28. The temporary connection 156 is not a threaded fastener coupling the humeral trial 30 to the adapter assembly 28. Advantageously, the temporary connection 156 between the humeral trial 30 and the adapter assembly 28 dramatically reduces trialing time by simplifying and shortening the process for changing out humeral trials 30. Unlike other implant assemblies, the humeral trial 30 may be changed out without disassembling the adapter assembly 28. This also means that the offset position 128 of the adapter plate 80 relative to the adapter 78 can be maintained when changing out humeral trials 30 and does not have to be reset each time a humeral trial 30 is changed out. Another added benefit is that the temporary connection 156 allows the medial humeral trial face 132 to be completely smooth just like the medial humeral implant face 140. Because there is no threaded fastener attaching the humeral trial 30 to the adapter assembly 28, the medial humeral trial 30 does not require an apical opening for receiving such a threaded fastener. Elimination of the apical opening from the humeral trial 30 is advantageous because it has been found that the apical opening on other humeral trials can catch on anatomical features of the shoulder joint or hardware during trialing and provide false range of motion feedback.

In FIGS. 5, 11, and 13-16, the temporary connection 156 shown is a magnetic connection between the humeral trial 30 and the adapter assembly 28. In accordance with this configuration, the adapter plate 80 includes one or more adapter plate magnets 158 that releasably hold the humeral trial 30 on the adapter plate 80. As illustrated, the adapter plate 80 includes one or more magnet cavities 160 that are open to the medial adapter plate face 114. These magnet cavities 160 in the adapter plate 80 each receive one of the adapter plate magnets 158 such that the adapter plate magnets 158 are embedded in the adapter plate 80. The humeral trial 30 may additionally include one or more humeral trial magnets 162 that releasably hold the humeral trial 30 on the adapter plate 80. As such, the humeral trial 30 may include one or more magnet cavities 160 that are open to the lateral humeral trial face 134. These magnet cavities 160 in the humeral trial 30 each receive one of the humeral trial magnets 162 such that the humeral trial magnets 162 are embedded in the humeral trial 30. Therefore several combinations exist, where the magnetic connection may include only the adapter plate magnets 158 in the adapter plate 80, only the humeral trial magnets 162 in the humeral trial 30, or both the adapter plate magnets 158 in the adapter plate 80 and the humeral trial magnets 162 in the humeral trial 30. Obviously, the number and placement of the magnets may vary from those shown in the figures without departing from the scope of the subject disclosure.

In contrast to the temporary connection 156 between the humeral trial 30 and the adapter assembly 28, a permanent connection 164 fixedly couples the humeral implant 32 to the adapter assembly 28. As the term is used herein, "permanent connection" encompasses any connection between the humeral implant 32 and the adapter assembly 28 that is designed or intended to remain in place post-surgery. For example and without limitation, such a permanent connection 164 could include a press fit between the humeral implant 32 and the adapter assembly 28 or an adhesive, glue, epoxy, binder, or cement connection between the humeral implant 32 and the adapter assembly 28. Therefore, it is conceivable that such a "permanent connection" could be separated by prying the humeral implant 32 from the adapter assembly 28 with a tool or other instrument or by breaking the humeral implant 32 and/or adapter assembly 28. In FIGS. 19 and 20, the permanent connection 164 shown is a press fit between the periphery 148 of the adapter plate 80 and the lateral humeral implant face 142 at the humeral implant cavity 144. Specifically, the periphery 148 of the adapter plate 80 and the lateral humeral implant face 142 at the humeral implant cavity 144 may each include complementary tapers 166 such that the adapter plate 80 becomes fixed to the humeral implant 32 when the adapter assembly 28 is pressed into the humeral implant cavity 144. Such complementary tapers 166 could be, without limitation, Morse tapers, which are well known permanent connections 164 in the field of surgical implant assemblies.

Figure 21:
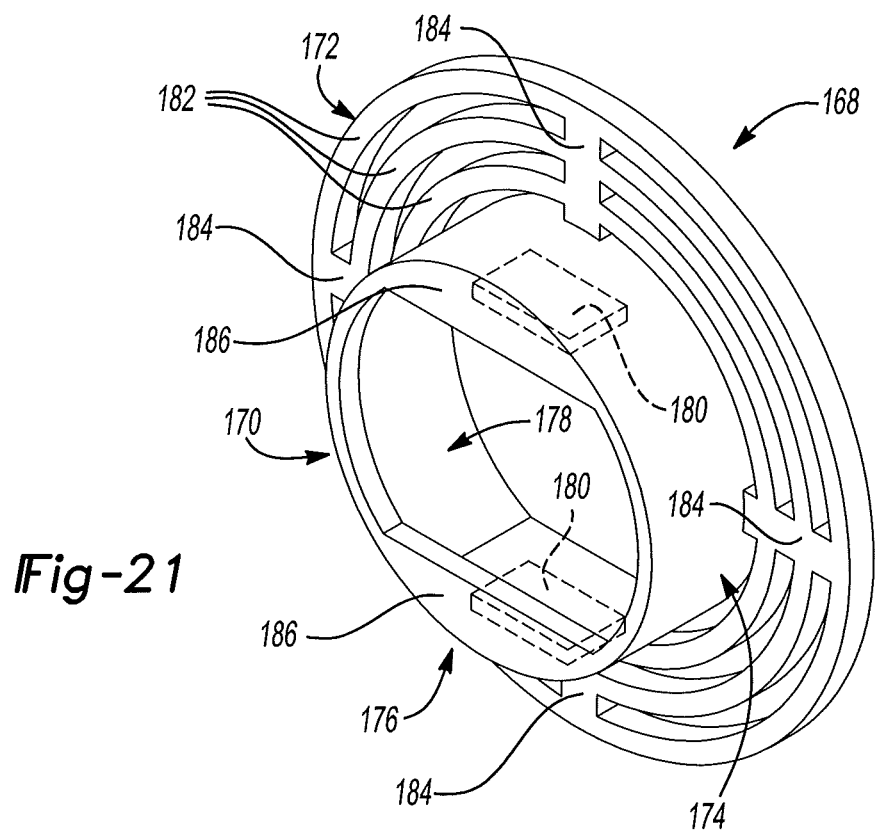
FIG. 21 is a front perspective view of an exemplary positioning guide of the exemplary humeral trial and implant assembly.
Figure 22:
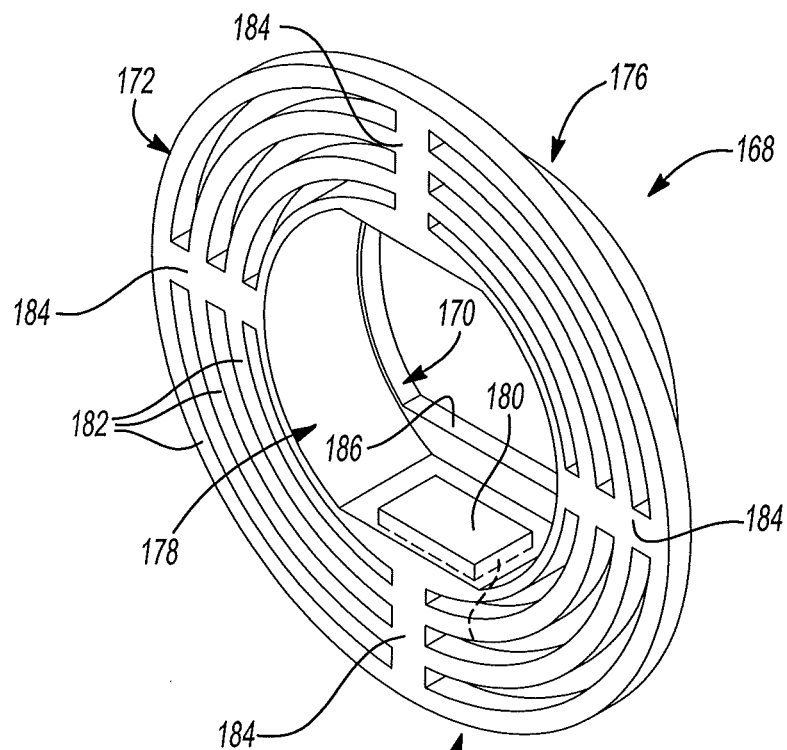
FIG. 22 is a rear perspective view of the exemplary positioning guide shown in FIG. 21.
Figure 23:
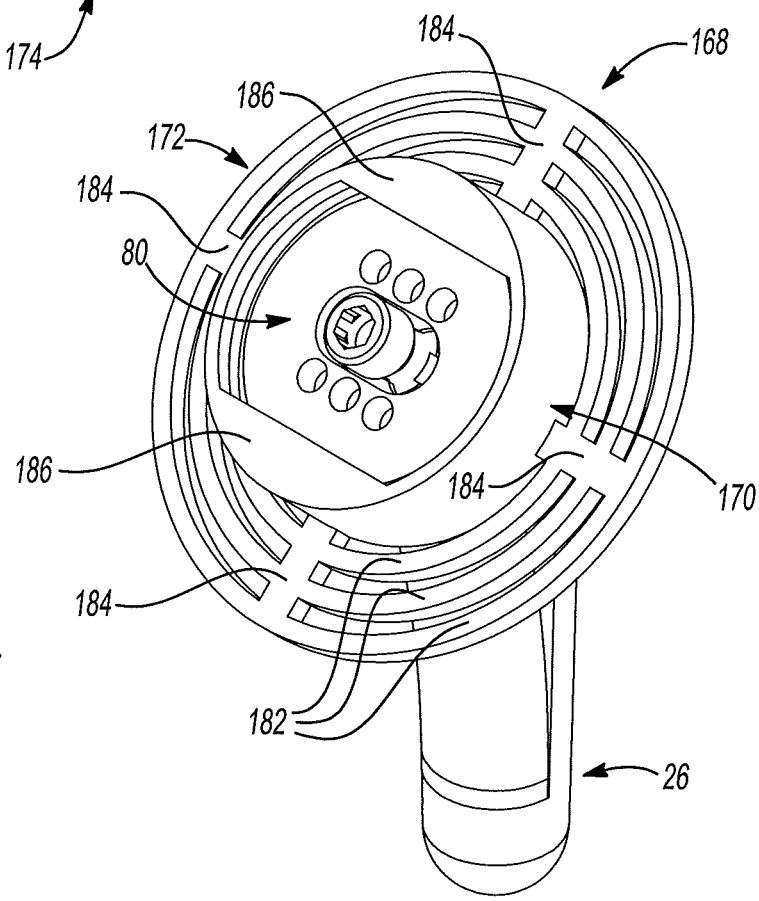
FIG. 23 is a front perspective view of the exemplary positioning guide of FIG. 21 shown installed on the exemplary adapter assembly of FIG. 5 and the humeral fixation component of FIG. 2.

Referring now to FIGS. 21-23, the humeral trial and implant assembly 20 may optionally include a positioning guide 168. The positioning guide 168 generally includes a hub 170 and a positioning guide flange 172 that extends outwardly from the hub 170. The hub 170 extends between a lateral hub end 174 and an medial hub end 176. The hub 170 has a hub cavity 178 that receives the adapter plate 80. As shown in FIG. 23, the hub cavity 178 mates with the periphery 148 of the adapter plate 80 when the humeral trial and implant assembly 20 is in the trialing configuration. Optionally, the positioning guide 168 may be magnetically retained on the adapter plate 80. In accordance with this configuration, the positioning guide 168 may include one or more positioning guide magnets 180 embedded in the hub 170 that releasably hold the positioning guide 168 on the adapter plate 80. Alternatively, the positioning guide 168 may be ferromagnetic such that the adapter plate magnets 158 hold the positioning guide 168 on the adapter plate 80.

The positioning guide flange 172 extends outwardly from the lateral hub end 174 and includes a plurality of annular rings 182 each representing different humeral trial/implant sizes. The plurality of annular rings 182 may be interconnected to one another and to the hub 170 by a plurality of spokes 184 that extend radially from the lateral hub end 174. Of course the positioning guide flange 172 may be constructed in other ways. By way of example and without limitation, the positioning guide flange 172 may be a solid disc and the plurality of annular rings 182 may be raised projections or other demarcations that are provided on the positioning guide flange 172. The positioning guide 168 may also include a medial wall 186 extending inwardly from the medial hub end 176 that abuts the medial adapter plate face 114 when the positioning guide 168 is placed on the adapter assembly 28. Accordingly, the medial adapter plate face 114 prevents over insertion of the adapter plate 80 in the hub cavity 178 of the positioning guide 168. It should be appreciated that the positioning guide 168 may be placed on the adapter plate 80 of the adapter assembly 28 after the humeral fixation component 26 has been installed on the humerus 22 and after the adapter assembly 28 has been assembled. With the positioning guide 168 fitted on the adapter plate 80, the surgeon inserts the body portion 86 of the adapter 78 into the primary bore 64 of the humeral fixation component 26. Then the surgeon uses the positioning guide 168 to determine the offset position 128 of the adapter plate 80 relative to the adapter 78 and a starting humeral trial/implant size. This process is done while shifting and rotating the positioning guide 168 relative to the humerus 22, which is accompanied by an associated shifting and rotation of the adapter assembly 28 relative to the humeral fixation component 26. Once a satisfactory offset position 128 is found, the surgeon then tightens the adapter fastener 82 thereby locking the offset position 128 of the adapter plate 80 in place relative to the adapter 78. The positioning guide 168 is then removed and the humeral trial 30 corresponding to the starting humeral trial/implant size is placed on the adapter assembly 28 for trialing.

It should be appreciated that the various components of the humeral trial and implant assembly 20 may be made of a wide variety of different materials. Often material selection is limited by health regulations that specify those materials which may be surgically implanted into the human body. Such heath regulations are often country specific and are often in a state of flux. In the exemplary configuration shown throughout the figures, the humeral fixation component 26, the various components of the adapter assembly 28, the humeral trial 30, the humeral implant 32, and the positioning guide 168 may be made from medical grade titanium, cobalt chrome, plastic, or a combination of these materials. Notwithstanding, it should be appreciated that these recitations of possible materials are merely exemplary and are not intended as limiting.

A method of using the humeral trial and implant assembly 20 set forth above in total shoulder arthroplasty is also provided. The method includes a plurality of steps, which are described below. The method includes installing a humeral fixation component 26 onto a humerus 22, optionally resurfacing an associated glenoid 24 with a glenoid resurfacing component 34, and assembling an adapter assembly 28 by installing an adapter plate 80 on an adapter 78. The step of assembling the adapter 78 may further include inserting an adapter flange 84 of the adapter 78 into a lateral adapter plate cavity 98 of the adapter plate 80 and inserting an adapter fastener 82 through a pass-through 124 in the adapter plate 80 and into an adapter bore 100 of the adapter 78 to couple the adapter plate 80 to the adapter 78. The step of inserting the adapter flange 84 into the lateral adapter plate cavity 98 may further include aligning a locking channel 104 disposed in the lateral adapter plate cavity 98 with an engagement member 106 that projects from the adapter flange 84 and inserting the engagement member 106 into the locking channel 104 to lock rotation of the adapter plate 80 relative to the adapter 78. In accordance with the above steps, the disclosed adapter assembly 28 may be assembled.

In accordance with the method, the step of inserting a body portion 86 of the adapter 78 into the primary bore 64 of the humeral fixation component 26 may be performed. As discussed above in the description of the humeral trial and implant assembly 20, the method may optionally include the steps of placing a positioning guide 168 over the adapter plate 80 where the positioning guide 168 has a plurality of annular rings 182 that each represent different humeral trial sizes and retaining the positioning guide 168 on the adapter plate 80 by magnetism. The method further includes positioning the adapter plate 80 relative to the humeral fixation component 26 by sliding the adapter plate 80 relative to the humeral fixation component 26 and the adapter 78 and tightening the adapter fastener 82 to lock the adapter plate 80 in place at a pre-determined offset position 128 relative to the humeral fixation component 26 and the adapter 78. Where the positioning guide 168 is used, the method may include the steps of using the plurality of annular rings 182 on the positioning guide 168 to help locate the pre-determined offset position 128 and then removing the positioning guide 168 from the adapter plate 80.

In accordance with the trialing procedure introduced above, the method includes the steps of placing a humeral trial 30 over the adapter plate 80 of the adapter assembly 28, retaining the humeral trial 30 on the adapter plate 80 by magnetism, positioning the humeral trial 30 adjacent the associated glenoid 24, and moving the humerus 22 through a range of motion and observing the fit and function of the humeral trial 30. It should be appreciated that the step of positioning the humeral trial 30 adjacent the associated glenoid 24 may include moving the humeral trial 30 into contact with the associated glenoid or moving the humeral trial 30 into contact with the glenoid resurfacing component 34. The step of determining whether the pre-determined position of the adapter plate 80 is appropriate and whether the humeral trial 30 is of appropriate size is performed based upon the observations made during the step of moving the humerus 22 through a range of motion. In accordance with this trialing procedure, the method includes removing the humeral trial 30 from the adapter plate 80 without disassembling the adapter assembly 28 and may further include repeating the steps of positioning the adapter plate 80, tightening the adapter fastener 82, placing the humeral trial 30 over the adapter plate 80, positioning the humeral trial 30 adjacent the associated glenoid 24, and moving the humerus 22 through the range of motion at different offset positions 128 of the adapter plate 80 in response to determining that the pre-determined offset position 128 of the adapter plate 80 previously used was not appropriate. Such reiterative steps are performed until a satisfactory offset position 128 is found. Similarly, the method may include repeating the steps of placing the humeral trial 30 over the adapter plate 80, positioning the humeral trial 30 adjacent the associated glenoid 24, and moving the humerus 22 through the range of motion with humeral trials 30 of varying sizes in response to determining that the humeral trial 30 previously used was not of appropriate size. Again, these reiterative steps are performed until a satisfactory humeral trial size is found.

The method additionally includes the steps of separating the adapter assembly 28 and the humeral fixation component 26 by removing the body portion 86 of the adapter 78 from the primary bore 64 of the humeral fixation component 26 and installing a humeral implant 32 on the adapter plate 80 of the adapter assembly 28. As discussed above, the step of installing the humeral implant 32 may further include pressing the humeral implant 32 onto the adapter plate 80 of the adapter assembly 28. The method also includes re-inserting the body portion 86 of the adapter 78 into the primary bore 64 of the humeral fixation component 26. This step of re-inserting the body portion 86 of the adapter 78 into the primary bore 64 may include pressing the body portion 86 of the adapter 78 into the primary bore 64 of the humeral fixation component 26 to create a press fit between the body portion 86 and the humeral fixation component 26. As a result of the press fit created during this step, the adapter assembly 28 and the humeral fixation component 26 are prevented from separating post-surgery. The method further includes the step of positioning the humeral implant 32 adjacent the associated glenoid 24. It should be appreciated that the order of the steps recited herein is exemplary in nature and is not intended to be limiting. Furthermore, it is envisioned that a variety of additional steps may be performed during surgery, either before, after, or during the method set forth above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. These antecedent recitations should be interpreted to cover any combination in which the inventive novelty exercises its utility. Many modifications and variations of the present invention are possible in light of the above teachings and may be practiced otherwise than as specifically described while within the scope of the appended claims.

What is claimed is:

1. A humeral trial and implant assembly for total shoulder arthroplasty comprising:
    a humeral fixation component including a primary bore, wherein said humeral fixation component is configured for fixation to a humerus;
    an adapter assembly including an adapter, said adapter including an adapter flange and a body portion extending from said adapter flange, wherein said body portion is received in said primary bore of said humeral fixation component;
    a humeral trial presenting a medial humeral trial face that has a bulbous shape and a lateral humeral trial face that defines a humeral trial cavity, wherein said humeral trial is coupled to said adapter assembly when said humeral trial is in a trialing configuration;
    a humeral implant presenting a medial humeral implant face that has a bulbous shape and a lateral humeral implant face that defines a humeral implant cavity, wherein said bulbous shape of said medial humeral implant face matches said bulbous shape of said medial humeral trial face, and wherein said humeral implant is coupled to said adapter assembly when said humeral implant is in an installed configuration;
    said adapter assembly including an adapter plate and an adapter fastener, said adapter plate coupled to said adapter, said adapter plate abutting said adapter flange, wherein said adapter plate and said adapter are discrete components, wherein said adapter plate is received in said humeral trial cavity when said humeral trial is in said trialing configuration, and wherein said adapter plate is received in said humeral implant cavity when said humeral implant is in said installed configuration, said adapter fastener coupling said adapter plate to said adapter, said adapter fastener including an adapter fastener head that tightens against said adapter plate and that is covered by said humeral trial when said humeral trial is in said trialing configuration;
    a temporary connection releasably coupling said humeral trial to said adapter assembly that provides separation of said humeral trial and said adapter assembly without requiring disassembly of said adapter assembly; and
    a permanent connection fixedly coupling said humeral implant to said adapter assembly.

2. A humeral trial and implant assembly as set forth in claim 1, wherein said temporary connection is a magnetic connection between said humeral trial and said adapter assembly.

3. A humeral trial and implant assembly as set forth in claim 2, wherein said magnetic connection includes at least one of an adapter plate magnet that is carried on said adapter plate or a humeral trial magnet that is carried on said humeral trial.

4. A humeral trial and implant assembly as set forth in claim 2, wherein said magnetic connection includes at least one adapter plate magnet carried on said adapter plate and at least one humeral trial magnet carried on said humeral trial.

5. A humeral trial and implant assembly as set forth in claim 1, wherein said permanent connection includes a press fit between said adapter plate and said humeral implant, said adapter plate and said humeral implant each including complementary tapers such that said adapter plate becomes fixed to said humeral implant when said adapter assembly is pressed into said humeral implant cavity.

6. A humeral trial and implant assembly as set forth in claim 1, further comprising:
a positioning guide including a hub and a positioning guide flange that extends outwardly from said hub, said hub defining a hub cavity that receives said adapter plate and said positioning guide flange having a plurality of annular rings each representing different humeral trial sizes.

7. A humeral trial and implant assembly as set forth in claim 6, wherein said positioning guide is magnetically retained on said adapter plate.

8. A humeral trial and implant assembly for total shoulder arthroplasty where said humeral implant is disposed between a humerus and a glenoid of a human body when said humeral implant is in an installed configuration, said humeral trial and implant assembly comprising:
a humeral fixation component configured to be surgically implanted into the humerus, said humeral fixation component including a primary bore;
an adapter assembly including an adapter, said adapter having a body portion that is received in said primary bore of said humeral fixation component;
a humeral trial presenting a medial humeral trial face that has a bulbous shape and a lateral humeral trial face that defines a humeral trial cavity, wherein said humeral trial is coupled to said adapter assembly when said humeral trial is in a trialing configuration;
a humeral implant presenting a medial humeral implant face that has a bulbous shape and a lateral humeral implant face that defines a humeral implant cavity, wherein said bulbous shape of said medial humeral implant face matches said bulbous shape of said medial humeral trial face, and wherein said humeral implant is coupled to said adapter assembly when said humeral implant is in the installed configuration;
said adapter assembly including an adapter plate, wherein said adapter plate is received in said humeral trial cavity when said humeral trial is in the trialing configuration, and wherein said adapter plate is received in said humeral implant cavity when said humeral implant is in the installed configuration, said adapter plate having a lateral adapter plate face, said lateral adapter plate face including a locking channel that extends into said adapter plate toward a medial adapter plate face, said locking channel having a linearly extending shape;
a magnetic connection releasably coupling said humeral trial to said adapter assembly; and
a permanent connection fixedly coupling said humeral implant to said adapter assembly.

9. A humeral trial and implant assembly as set forth in claim 8, further comprising a glenoid resurfacing component presenting a lateral surface and a medial surface, wherein said lateral surface of said glenoid resurfacing component abuts said medial humeral trial face when said humeral trial is in the trialing configuration, wherein said lateral surface of said glenoid resurfacing component abuts said medial humeral implant face when said humeral implant is in the installed configuration, and wherein said medial surface of said glenoid resurfacing component is configured to abut the glenoid when said humeral trial is in the trialing configuration and when the humeral implant is in the installed configuration.

10. A humeral trial and implant assembly for total shoulder arthroplasty where said humeral trial and implant assembly is disposed between a humerus and a glenoid of a human body, said humeral trial and implant assembly comprising:
a humeral fixation component including a primary bore that extends into said humeral fixation component;
an adapter assembly including an adapter and an adapter plate;
said adapter including an adapter bore, an adapter flange presenting a medial adapter flange face and a lateral adapter flange face, and a body portion extending from said lateral adapter flange face, wherein said body portion is received in said primary bore of said humeral fixation component;
a humeral trial presenting a medial humeral trial face that has a bulbous shape and a lateral humeral trial face that defines a humeral trial cavity, wherein said humeral trial is coupled to said adapter assembly when said humeral trial is in a trialing configuration;
a humeral implant presenting a medial humeral implant face that has a bulbous shape and a lateral humeral implant face that defines a humeral implant cavity, wherein said bulbous shape of said medial humeral implant face matches said bulbous shape of said medial humeral trial face, and wherein said humeral implant is coupled to said adapter assembly when said humeral implant is in an installed configuration;
said adapter plate abutting said medial adapter flange face, wherein said adapter plate is received in said humeral trial cavity when said humeral trial is in said trialing configuration, and wherein said adapter plate is received in said humeral implant cavity when said humeral trial is in said installed configuration;
said adapter plate presenting a medial adapter plate face and a lateral adapter plate face, said lateral adapter plate face including a locking channel that extends into said adapter plate toward said medial adapter plate face; and
said adapter including an engagement member projecting from said medial adapter flange face that is received in and engages said locking channel of said adapter plate to prevent rotation of said adapter plate relative to said adapter when said humeral trial is in said trialing configuration and when said humeral implant is in said installed configuration.

11. A humeral trial and implant assembly as set forth in claim 10, wherein said locking channel of said adapter plate and said engagement member of said adapter flange each have a linearly extending shape.

12. A humeral trial and implant assembly as set forth in claim 11, wherein said lateral adapter plate face defines a lateral adapter plate cavity that receives said adapter flange, wherein said lateral adapter plate cavity is larger than said adapter flange and is elongated along an offset direction, and wherein said offset direction is parallel to said locking channel and said engagement member such that said adapter may be shifted relative to said adapter plate in said offset direction when said humeral trial is in said trialing configuration.

13. A humeral trial and implant assembly as set forth in claim 12, wherein said adapter plate includes a pass-through that extends between and that is open to said medial adapter plate face and said lateral adapter plate cavity.

14. A humeral trial and implant assembly as set forth in claim 13, wherein said adapter assembly includes an adapter fastener that extends through said pass-through and into said adapter bore to selectively fix said adapter plate to said adapter and wherein said pass-through is elongated along said offset direction such that said adapter may be shifted relative to said adapter plate in said offset direction when said humeral trial is in said trialing configuration, said adapter fastener having an adapter fastener head that tightens against said adapter plate to fix said adapter plate in place relative to said adapter at an offset position located along said offset direction.

15. A humeral trial and implant assembly as set forth in claim 14, further comprising:
a temporary connection releasably coupling said humeral trial to said adapter assembly that provides separation of said humeral trial and said adapter assembly while maintaining said offset position of said adapter plate relative to said adapter and without requiring disassembly of said adapter assembly.

16. A humeral trial and implant assembly as set forth in claim 12, wherein said lateral adapter plate cavity has at least one planar side that is parallel with said offset direction and wherein said adapter flange has a perimeter including at least one flat section that abuts said at least one planar side of said lateral adapter plate cavity to prevent rotation of said adapter plate relative to said adapter.

17. A humeral trial and implant assembly as set forth in claim 10, wherein said adapter plate is coupled to said adapter and wherein said adapter plate and said adapter are discrete components of said adapter assembly.

18. A humeral trial and implant assembly as set forth in claim 10, wherein said medial adapter plate face is disposed within said humeral trial cavity adjacent said lateral humeral trial face when said humeral trial is in said trialing configuration and is disposed in said humeral implant cavity adjacent said lateral humeral implant face when said humeral implant is in said installed configuration.

19. A humeral trial and implant assembly for total shoulder arthroplasty comprising:
a humeral fixation component including a primary bore, wherein said humeral fixation component is configured for fixation to a humerus;
an adapter assembly including an adapter, said adapter including an adapter flange and a body portion extending from said adapter flange, wherein said body portion is received in said primary bore of said humeral fixation component;
a humeral trial presenting a medial humeral trial face that has a bulbous shape and a lateral humeral trial face that defines a humeral trial cavity, wherein said humeral trial is coupled to said adapter assembly when said humeral trial and implant assembly is in a trialing configuration;
a humeral implant presenting a medial humeral implant face that has a bulbous shape and a lateral humeral implant face that defines a humeral implant cavity, wherein said bulbous shape of said medial humeral implant face matches said bulbous shape of said medial humeral trial face, and wherein said humeral implant is coupled to said adapter assembly when said humeral trial and implant assembly is in an installed configuration;
said adapter assembly including an adapter plate coupled to said adapter, said adapter plate abutting said adapter flange, wherein said adapter plate and said adapter are discrete components, wherein said adapter plate is received in said humeral trial cavity when said humeral trial is in said trialing configuration, and wherein said adapter plate is received in said humeral implant cavity when said humeral implant is in said installed configuration;
a temporary connection releasably coupling said humeral trial to said adapter assembly that provides separation of said humeral trial and said adapter assembly without requiring disassembly of said adapter assembly;
a permanent connection fixedly coupling said humeral implant to said adapter assembly, and
a positioning guide including a hub and a positioning guide flange that extends outwardly from said hub, said hub defining a hub cavity that receives said adapter plate and said positioning guide flange having a plurality of annular rings each representing different humeral trial sizes.

20. A humeral trial and implant assembly as set forth in claim 19, wherein said positioning guide is magnetically retained on said adapter plate.

* * * * *

UNITED STATES PATENT AND TRADEMARK OFFICE
CERTIFICATE OF CORRECTION

PATENT NO.        : 9,597,191 B2
APPLICATION NO.   : 14/678071
DATED             : March 21, 2017
INVENTOR(S)       : Muir et al.

Page 1 of 1

It is certified that error appears in the above-identified patent and that said Letters Patent is hereby corrected as shown below:

In the Claims

In Column 22, Line 30, in Claim 19, delete "assembly," and insert --assembly;-- therefor Signed and Sealed this
Twenty-fourth Day of April, 2018

Andrei Iancu
*Director of the United States Patent and Trademark Office*